(12) United States Patent
Mansy et al.

(10) Patent No.: US 6,443,907 B1
(45) Date of Patent: Sep. 3, 2002

(54) ACOUSTIC DETECTION OF RESPIRATORY CONDITIONS

(75) Inventors: Hussein A. Mansy, Justice; Richard H. Sandler, Evanston, both of IL (US)

(73) Assignee: Biomedical Acoustic Research, Inc., Evanston, IL (US)

( * ) Notice: Subject to any disclaimer, the term of this patent is extended or adjusted under 35 U.S.C. 154(b) by 7 days.

(21) Appl. No.: 09/684,068

(22) Filed: Oct. 6, 2000

(51) Int. Cl.[7] .............................. A61B 5/08; A61B 7/00
(52) U.S. Cl. ...................................... 600/529; 600/586
(58) Field of Search ................................ 600/529, 586, 600/587, 552, 553, 530, 531, 532, 533, 534, 535, 538, 437, 438

(56) References Cited

U.S. PATENT DOCUMENTS

| | | | |
|---|---|---|---|
| 3,990,435 A | * 11/1976 | Murphy | 600/529 |
| 4,008,711 A | 2/1977 | Olinger et al. | |
| 4,052,977 A | 10/1977 | Kay | |
| 4,672,977 A | 6/1987 | Kroll | |
| 4,689,986 A | 9/1987 | Carson et al. | |
| 4,928,697 A | 5/1990 | Hsu | |
| 5,165,417 A | * 11/1992 | Murphy, Jr. | 600/529 |
| 5,259,384 A | 11/1993 | Kaufman et al. | |
| 5,309,922 A | 5/1994 | Schechter et al. | |
| 5,445,144 A | 8/1995 | Wodicka et al. | |
| 5,515,865 A | * 5/1996 | Scanlon | 600/534 |
| 5,588,439 A | * 12/1996 | Hollub | 600/534 |
| 5,638,824 A | * 6/1997 | Summers | 600/534 |
| 5,701,912 A | 12/1997 | Greening et al. | |
| 5,718,227 A | 2/1998 | Witlin et al. | |
| 5,816,245 A | 10/1998 | Manseur et al. | |
| 5,989,193 A | * 11/1999 | Sullivan | 600/534 |
| 6,168,568 B1 | * 1/2001 | Gavriely | 600/529 |

OTHER PUBLICATIONS

Bohadana et al., "Transmission of Sound Generated by Sternal Percussion," *J. Appl. Physiol.*, 66(1):273–277 (1989).

(List continued on next page.)

*Primary Examiner*—Kevin Shaver
*Assistant Examiner*—Navin Natnithithadha
(74) *Attorney, Agent, or Firm*—Marshall, Gerstein & Borun

(57) ABSTRACT

Diagnostic techniques are provided to enable the detection of a respiratory condition within a patient's body. The diagnostic techniques compare the acoustic generation and transmission characteristics of the patient's chest and lungs to reference acoustic characteristics and/or predetermined threshold values to determine if an abnormal respiratory condition is present within the patient. The diagnostic techniques process sound waves or vibrations that have interacted with a respiratory condition within a patient and which impinge on the chest wall of the patient. The sound waves or vibrations may be initiated by a speaker that emits sounds waves into the mouth and trachea of the patient or may be indigenous sounds. Alternatively, the sounds waves or vibrations may be initiated using percussive inputs to the chest wall of the patient. In processing the sound waves, the diagnostic techniques calculate energy ratios using energy values within high and low frequency bands, signal time delays, and/or dominant frequencies and compare the calculated values to predetermined reference thresholds to generate outputs indicative of the respiratory condition within the patient.

67 Claims, 10 Drawing Sheets

OTHER PUBLICATIONS

Bourke et al., "Percussion of the Chest Re–Visited: A Comparison of the Diagnostic Value of Auscultatory and Conventional Chest Percussion," *I.J.M.S.*, pp. 82–84 (1989).

Donnerberg et al., "Sound Transfer Function of the Congested Canine Lung," *Br. J. Dis. Chest*, 74:23–31 (1980).

Gavriely et al., "Spectral Characteristics of Normal Breath Sounds," *J. Appl. Physiol.:Respirat.. Environ. Exercise Physiol.*, 50(2):307–314 (1981).

Gilbert, V.E., "Shifting Percussion Dullness of the Chest: A Sign of Pleural Efusion," *Southern Medical Journal*, 90(12):1255–1256.

Goncharoff et al., "Wideband Acoustic Transmission of Human Lungs," *Med. & Biol. Eng. & Comput.*, 27:513–519 (Sep. 1989).

Guarino, J.R., "Auscultatory Percussion of the Chest," *The Lancet*, pp. 1332–1334 (Jun. 21, 1980).

Kraman et al., "Transmission to the Chest of Sound Introduced at the Mouth," *J. Appl. Phusiol.*, 66(1):278–281 (1989).

Mansfield et al., "An Acoustical Guidance and Position Monitoring System for Eddotracheal Tubes," *IEEE Transactions on Biomedical Engineering*, 40(12): 1330–1335 (Dec. 1993).

Pasterkamp et al., "Lung Sound Spectra at Standardized Air Flow in Normal Infants, Children, and Adults," *Am. J. .Respir. Crit. Care Med.*, 154:424–430 (1996).

Ploy–Song–Sang et al., "Distribution of Regional Ventilation Measured by Breath Sounds," *Am. Rev. Respir. Dis.*, 117:657–664 (1987).

Wodicka et al., "Transfer Function of Sound Transmission in Subglottal Human Respiratory System at Low Frequencies," *J. Appl. Physiol.*, 69(6):2126–2130 (1990).

Wodicka et al., "Spectral Characteristics of Sound Transmission in the Human Respiratory System," *IEEE Transactions on Biomedical Engineering*, 37(12):1130–1135 (Dec. 1990).

Wodicka et al., "Phase Delay of Pulmonary Acoustic Transmission from Trachea to Chest Wall," *IEEE Tranactions on Biomedical Engineering*, 39(10):1053–1059 (Oct. 1992).

Mansy et al., "Method and Apparatus for Detection of Air Cavities in a Body," U.S. Serial No. 09/050,716, filed on Mar. 30, 1998.

* cited by examiner

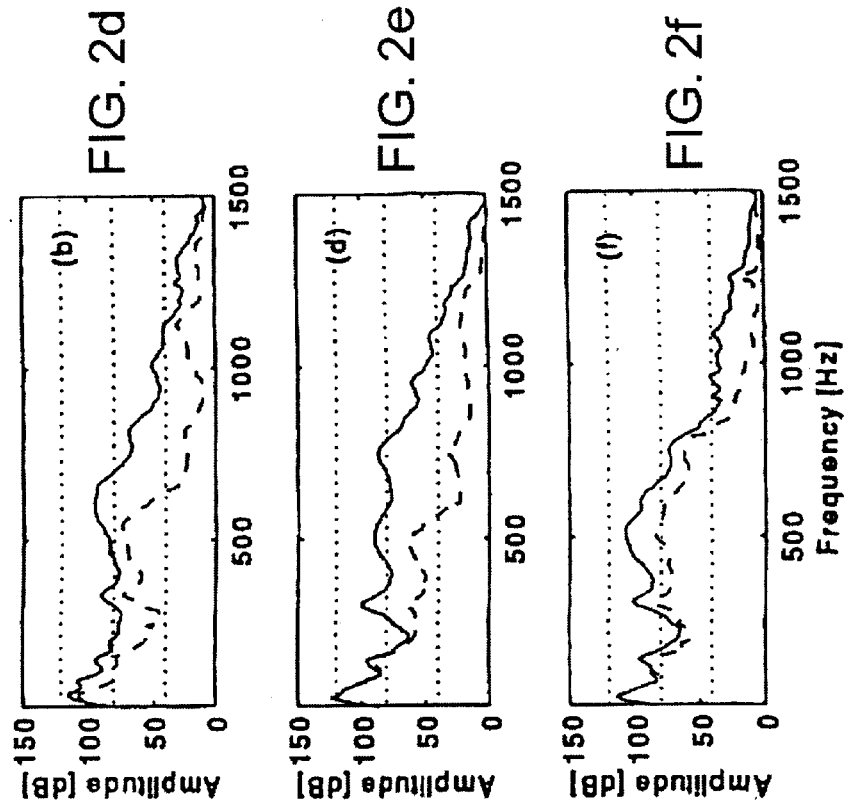
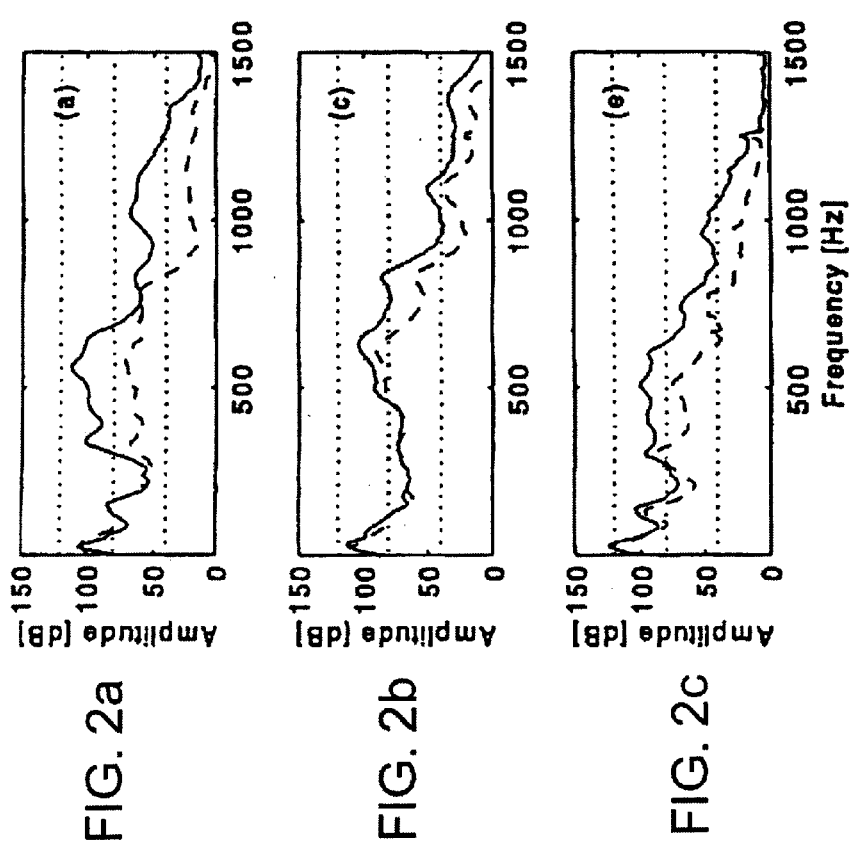

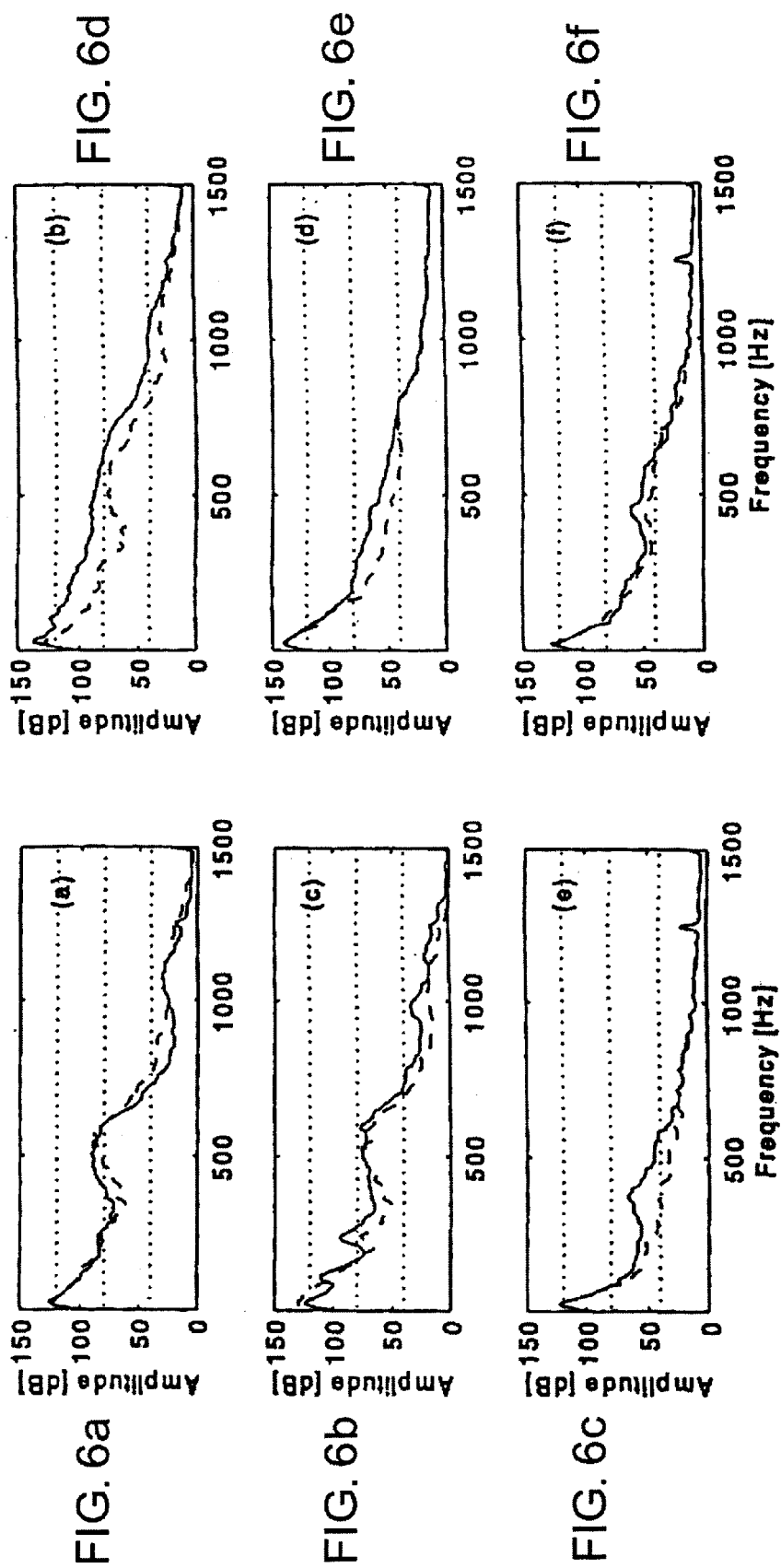

ACOUSTIC DETECTION OF RESPIRATORY CONDITIONS

BACKGROUND OF THE INVENTION

1. Field of the Invention

The invention relates generally to the non-invasive diagnosis of conditions within a human or animal body and, more particularly, the invention relates to diagnostic techniques that use the acoustic characteristics within a body to detect respiratory conditions therein.

2. Description of Related Technology

One particularly problematic respiratory condition is pneumothorax. Generally speaking, pneumothorax refers to the formation of a gas cavity between one or both lungs and the chest wall. As is well known, pneumothorax has many potential causes, including, for example, spontaneous rupture of small alveoli or blebs, progression of inflammatory diseases, complications of diagnostic or therapeutic procedures, penetrating wounds caused by a knife, bullet, etc. and blunt chest trauma, which may be, for example, caused by motor vehicle accidents. Although trauma is a significant cause of pneumothorax, severe chest wall injury is often difficult to detect based on the outward appearance of a patient's body and, as a result, the diagnosis of pneumothorax is often missed in these cases.

Pneumothorax also occurs in 5–15% of mechanically ventilated patients, and other iatrogenic pneumothoraces are becoming more common with the increasing use of chest invasive procedures such as central venous line insertions, which are often used for monitoring and fluid replacement in emergency trauma cases, and percutaneous transthoracic lung biopsies. For these invasive procedures, the pneumothorax rates are about 5% and 20%, respectively. It is estimated that over 50,000 cases of pneumothorax occur each year in the United States and, thus, more effective diagnosis of pneumothorax could significantly reduce morbidity and mortality.

Conventional pneumothorax diagnostic techniques are typically based on patient history, physical examination of the patient, chest x-rays (CXRs), computerized tomogram (CT) and ultrasound. Patient history, physical examination and CXRs are the techniques most commonly employed to diagnose pneumothorax. Unfortunately, patient history and physical examination are typically unreliable techniques for diagnosing pneumothorax because the symptoms associated with pneumothorax are also present in a number of unrelated clinical conditions such as cardiac ischemia, pneumonia, pulmonary embolism, esophageal spasm/reflux, and musculoskeletal strain. As a result, diagnosis of pneumothorax based on patient history and/or physical examination is very difficult and, in many cases, virtually impossible. For example, one study reported that physical examinations resulted in misdiagnosis in 42% of patients having a pneumothorax condition that arose from a penetrating chest wound.

Percussion is one common physical examination technique used by physicians to diagnose a variety of chest abnormalities. Most studies of percussion rely on qualitative descriptions such as "dull" and "resonant" to describe the chest sounds resulting from a percussive input to the patient's chest. Reported percussion response waveforms of a normal chest are typically 20 milliseconds (ms) long and contain an initial spike followed by a decaying waveform with spectral peaks in the 70 Hertz (Hz) –200 Hz range. Using percussion, skilled physicians have noted "hyperresonance" as an acoustic phenomenon that is often heard in patients having a pneumothorax condition. In addition, acoustic asymmetries with large pneumothoraces have been reported when manually percussing both clavicles in turn while auscultating (i.e., listening to) the sternum. In any event, despite widespread belief in the usefulness of percussive techniques, uncertainty of its diagnostic capability exits because of the inherent dependence on the skill of the operator and their personal perception of the sound qualities of a patient's chest response.

Misdiagnosis of pneumothorax may also occur when using CXRs and CT due to large bullae and cysts within the lung or pleural space, patient clothing, tubing, skin folds, and chest wall artifacts. Additionally, with CXRs, patients are exposed to potentially harmful doses of radiation. Unfortunately, the radiation problem is compounded by the fact that CXRs are often performed unnecessarily (which needlessly exposes patients to radiation) because physicians are unwilling to miss the diagnosis due to the life threatening nature of pneumothorax, its tendency to progress rapidly to tension pneumothorax and the ease with which pneumothorax can be treated if detected. As a result, CXRs are ordered as a precautionary measure for many patients that do not actually have pneumothorax. Further, because each patient with pneumothorax is typically subjected to multiple CXRs to generate subsequent films that document relative improvement, it is estimated that the total number of pneumothorax diagnostic tests conducted each year in the U.S. may be hundreds of thousands.

To overcome the diagnostic limitations of CXRs and CT, patients may be placed in the upright or lateral decubitus positions, and/or end-expiratory exposures may be used instead. Unfortunately, these positioning maneuvers are typically difficult to perform on critically ill patients. In addition to patient positioning difficulties, a common limitation of CXRs and CT is the difficulty and danger of transporting a critically ill patient to the imaging suite and the lack of equipment and staff availability in a timely manner, which is typically the case at night or in remote areas (such as, for example, battlefield conditions, the scene of an accident, a bedside, etc.). Further, CXRs, CT and other conventional imaging techniques typically involve a significant amount of delay between the examination of a patient and the availability of diagnostic results. Such a delay may be unacceptable in many situations, particularly where the patient's condition is critical or life-threatening. Still further, as is commonly known, diagnostic techniques based on ultrasound suffer from a high false positive rate due to inherent limitations.

Some researchers have used zero radiation techniques that rely on external low frequency forcing to non-invasively diagnose lung diseases other than pneumothorax. For example, Wodicka et al. [Wodicka GR, Aguirre A, DeFrain PD, and Shannon DC, *Phase Delay of Pulmonary Acoustic Transmission from Trachea to Chest Wall*, IEEE Transactions on Biomedical Engineering 1992; 39:1053–1059] and Kraman et al. [Kraman SS, Bohandana AB, *Transmission to the Chest of Sound Introduced at the Mouth*, J Applied Physiology, 1989;66:278–281] studied acoustic transmission characteristics from the trachea to the chest wall by introducing low frequency sound waves at the mouth and measuring the sound waves received at the chest Wall. The Wodicka et al. study found that geometrical changes within the lung cause sound transmission times to be frequency dependent because different wavelengths of sound couple to different parts of the lung lining. The Kraman et al. study found that changes in the lung volume or the resident gas composition did not consistently alter the peak-to-peak amplitude or the peak frequency of the measured signal. On the other hand, Donnerberg et al. [Donnerberg RL, Druzgalski CK, Hamlin RL, Davis GL, Campbell RM, Rice DA. British J, *Diseases of the Chest* 1980;74:23–31] studied the sound transfer function in normal and congested dog lungs using a technique similar to that described by Wodicka et al. and found a consistent increase in the transmitted sound as the lung wet-to-dry weight ratio increased.

Another abnormal respiratory condition that typically occurs in patients in ambulances and operating rooms is the misplacement of an endotracheal (ET) tube within a patient's trachea. As is generally known, ET tubes are placed in patients to establish an open airway, deliver anesthetic agents, and/or to perform mechanical ventilation. Typically, when an ET tube is misplaced, it travels too far into one of the two main bronchi (i.e., left and right) and blocks the other bronchus partially or completely, thereby limiting or eliminating ventilation into the lung associated with the obstructed bronchus. ET tube misplacement may also occur after the ET tube has been initially properly placed. For example, the ET tube may spontaneously move due to movements of the patient and/or movements of the ventilator tubing attached to the ET tube. Additionally, an ET tube may be misplaced into the esophagus of a patient or may be misplaced as a result of extubation.

Typically, ET tube placement is checked using x-ray or carbon dioxide measurements. However, carbon dioxide based detection techniques provide limited accuracy and the time, cost and radiation exposure associated with x-rays limits the usefulness of x-ray based detection of ET tube misplacement, especially when multiple or on-line monitoring of the ET tube placement is desired.

SUMMARY OF THE INVENTION

Diagnostic techniques are provided to enable the detection of a respiratory condition within a patient's body. Generally speaking, the diagnostic techniques described herein use the acoustic characteristics of a patient's lungs and chest to determine if a respiratory condition is present. More specifically, the diagnostic techniques described herein compare the acoustic generation and transmission characteristics of the patient's chest and lungs to reference acoustic characteristics and/or predetermined threshold values to determine if an abnormal respiratory condition is present within the patient. In particular, the diagnostic techniques described herein can be used, for example, to detect the presence of a gas cavity between one or more of a patient's lungs and chest wall, which is symptomatic of a pneumothorax condition. Alternatively, the diagnostic techniques described herein can be used, for example, to detect a relative difference between the acoustic transmission characteristics from a patient's trachea to the left and right lungs, which is symptomatic of an ET tube blocking (or partially blocking) one of the patient's bronchi.

In accordance with one aspect of the invention a system and method for detecting a respiratory condition within a body emits sound waves into a first location of the body and converts the emitted sound waves into a first electrical signal. The system and method receives vibrations resulting from the sound waves interacting with the respiratory condition and impinging on a second location of the body, converts the received vibrations into a second electrical signal and uses the first and second electrical signals to calculate a value indicative of the respiratory condition.

Additionally, the system and method may generate a first set of frequency data using the first electrical signal and may further generate a second set of frequency data using the second electrical signal. The system and method may calculate transfer function data using the first and second sets of frequency data and may use the transfer function data to calculate an energy ratio indicative of the respiratory condition.

In some embodiments, the system and method may calculate the energy ratio indicative of the respiratory condition based on a first energy within a first band of frequencies and a second energy within a second band of frequencies. Still further, the system and method may define the first band of frequencies to include higher frequency components than the second band of frequencies.

In accordance with another aspect of the invention, a system and method for detecting a respiratory condition within a body receives indigenous respiratory sounds adjacent to a first location of the body at a first time and converts the indigenous respiratory sounds received at the first time into a first electrical signal. Additionally, the system and method generates a first set of frequency data using the first electrical signal and uses the first set of frequency data to calculate an energy ratio indicative of the respiratory condition.

Still further, the system and method may calculate the energy ratio indicative of the respiratory condition based on a first energy within a first band of frequencies and a second energy within a second band of frequencies. In some embodiments, the system and method may define the first band of frequencies to include higher frequency components than the second band of frequencies.

In accordance with still another aspect of the invention a system and method of detecting a respiratory condition within a body impacts a portion of the body and receives vibrations resulting from the impact interacting with the respiratory condition and the impacted portion of the body. Further, the system and method converts the received vibrations into an electrical signal and uses the electrical signal to calculate a value indicative of the respiratory condition.

In some embodiments, the system and method calculates an envelope of the electrical signal and uses the envelope to calculate a characteristic of the envelope of the electrical signal. The system and method may calculate the characteristic of the envelope of the electrical signal by identifying a temporal location associated with a maximum amplitude of the envelope of the electrical signal, identifying a portion of the envelope of the electrical signal surrounding the temporal location associated with the maximum amplitude of the envelope of the electrical signal and calculating the characteristic of the envelope of the electrical signal using the identified portion of the envelope of the electrical signal.

BRIEF DESCRIPTION OF THE DRAWINGS

FIGS. 2a–2f are exemplary graphical representations of the acoustic response characteristics of six test subjects measured from their mouths to their chest walls;

FIGS. 6a–6f are exemplary graphical representations showing spectra of indigenous respiratory sounds for normal and pneumothorax states within six test subjects;

FIG. 7b is an exemplary graphical representation showing spectra of indigenous respiratory sounds for an abnormal respiratory condition in which an ET tube has migrated into the right bronchus of the test subject of FIG. 7a;

DETAILED DESCRIPTION OF THE PREFERRED EMBODIMENTS

A pneumothorax condition results in the presence of a gas cavity in the pleural space that separates the lung parenchyma and the chest wall. At frequencies below 10 kilohertz (kHz) sound wavelengths significantly exceed alveolar size and the lung parenchyma acts as a foam-like substance made of a mixture of air and soft tissue. At frequencies below 10 kHz, predominantly compression wave propagation is supported and because the composite density of the lung is dominated by the tissue component, the resulting speed of sound through the lung parenchyma is low (e.g., 25–70 meters per second (m/s)), which is much lower than the speed of sound in free air and soft tissue (i.e., 330 m/s and 1500 m/s, respectively). This large difference in sound speed and in mass density (of air compared to tissue) combine to create a relatively large acoustic impedance mismatch between the lung tissue and the gas cavity. Thus, when sound waves introduced at the patient's mouth travel through the airways and the lung parenchyma to the chest wall, this impedance mismatch causes a large decrease (typically 20–30 dB) in the amplitude (i.e., an attenuation) of the sound waves received at the chest wall.

Figure 1:
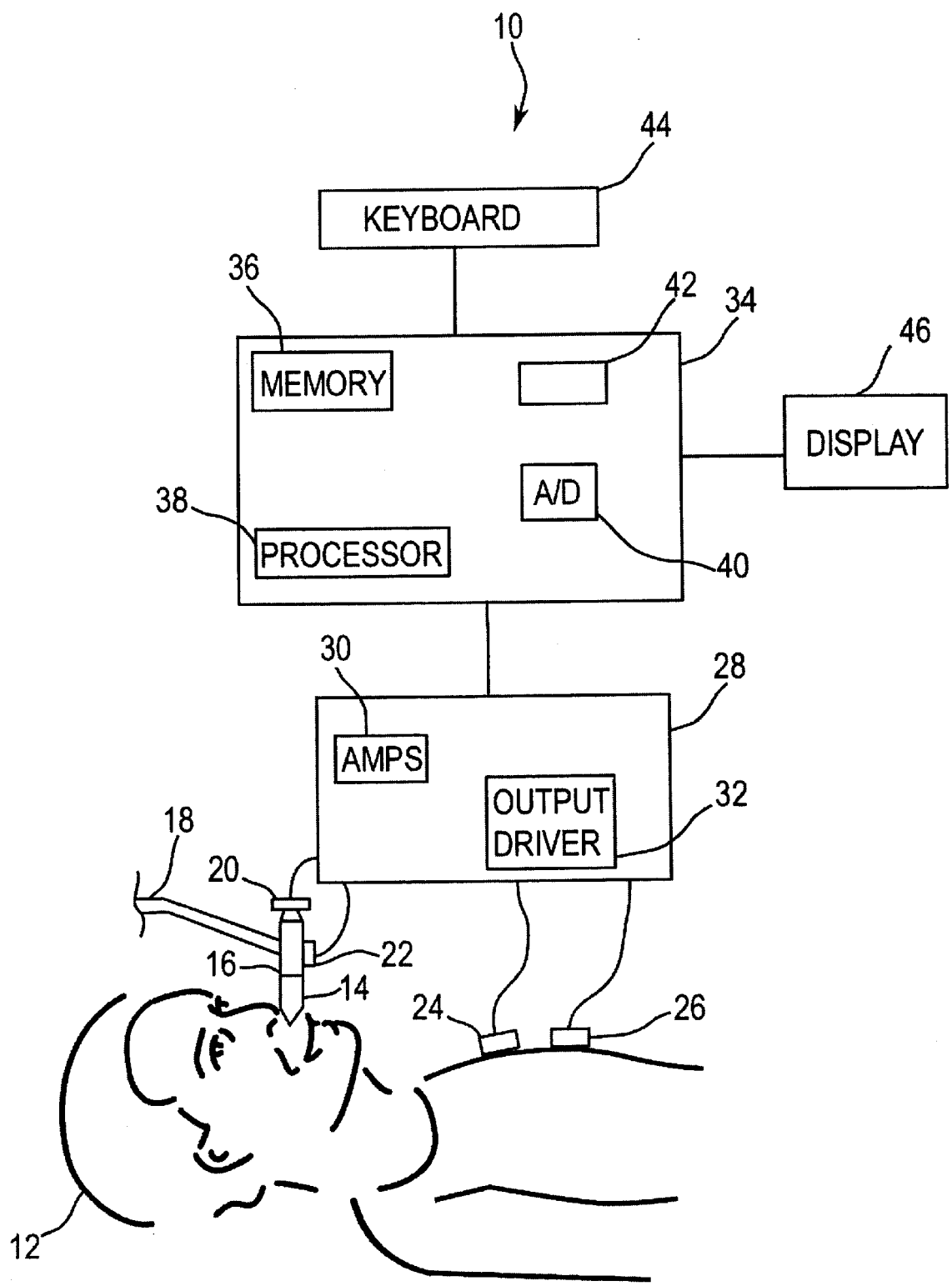
FIG. 1 is an exemplary schematic block diagram illustrating a system for measuring the acoustic response characteristics from the mouth to the chest wall of an endotracheally intubated patient.

FIG. 1 is an exemplary schematic block diagram illustrating a system 10 for measuring the acoustic response characteristics from the mouth to the chest wall of an endotracheally intubated patient 12. As shown in FIG. 1, an endotracheal (ET) tube 14 is inserted into the mouth and trachea of the patient 12 in a conventional manner. A "T" shaped tube 16 (hereinafter referred to as a "T-tube") is axially aligned with and is coupled to the ET tube 14 to enable a ventilator output tube 18 to provide a supply of air to the patient 12. A speaker 20, or any other suitable actuator, is coupled to the T-tube 16 and may be driven to produce sound waves, which may or may not be in the audible range (i.e., 20 Hz–20 kHz), that are conducted by the T-tube 16 and the ET tube 14 into the mouth and trachea of the patient 12. Additionally, a microphone 22, or any other suitable sensor that detects acoustic vibrations, is coupled to the T-tube 16 so that the sounds produced by the speaker 20 can be monitored and/or so that sounds emanating from the trachea of the patient 12 can be detected, if desired.

Surface sensors 24 and 26 are adjacent to, and preferably in contact with, the chest of the patient 12 and are configured to detect and measure sound waves impinging on the chest wall of the patient 12. The surface sensors 24 and 26 may be electronic stethoscopes, air-coupled microphones, accelerometers, contact microphones, capacitive or optical vibration sensors, or any other transducer that converts vibrations or sound waves into electrical signals.

The surface sensors 24 and 26, the microphone 22, and the speaker 20 are electrically coupled to a signal conditioning unit 28 that includes amplifiers 30 and an output driver 32. The amplifiers 30 receive low-level signals from the microphone 22 and one or more of the surface sensors 24 and 26 and convert these low-level signals into high-level signals, which are coupled to a processing unit 34. The output driver 32 receives and converts low power signals from the processing unit 34 into signals that are suitable for driving the speaker 20, which is typically a low impedance device having an inductive load characteristic.

The processing unit 34 includes a memory 36, a processor 38, an analog-to-digital converter (A/D) 40 and a plurality of software routines 42 that may be stored on the memory 36 and executed by the processor 38 to perform the diagnostic techniques described herein. The processing unit 34 may be based on a variety of commercially available platforms such as a personal computer or a workstation, or may be based on a custom platform that uses application-specific integrated circuits (ASICs) and other custom circuitry to carry out the diagnostic techniques described herein. Additionally, the processing unit 34 is coupled to one or more input/output (I/O) devices that enable a user to interface to the system 10. By way of example only, the processing unit 34 may receive user inputs via a keyboard 44 or any other data input device and may provide graphical displays to the user via a display unit 46, which may be, for example, a conventional video monitor.

In operation, the system 10 shown in FIG. 1 is controlled by the processing unit 34 to respond to user inputs, which, for example, may cause the processing unit 34 to begin execution of one or more of the software routines 42, thereby enabling the user to acoustically detect a respiratory condition within the patient 12. By way of example only, the processing unit 34 may execute one of the software routines 42 that provides a signal to the output driver 32 of the signal conditioning unit 28, which in turn drives the speaker 20 to produce sound waves. These sound waves may, for example, include frequency components of uniform amplitude over a 20 Hz to 1600 Hz range. However, sound waves including other frequency ranges and having different amplitude characteristics may be used without departing from the scope and the spirit of the invention.

In any event, the sound waves generated by the speaker 20 travel through the T-tube 16, the ET tube 14 and into the mouth and trachea of the patient 12. Alternatively, in the case of a non-intubated patient, the sound waves generated by the speaker 20 may be directed into the mouth of the patient using a mask and/or a mouthpiece rather than the ET tube 14. In the case where a mask and/or mouthpiece is used to direct the sounds waves into the patient's mouth, a nasal clip may also be used to encourage oral airway patency. However, in the case where the patient is unconscious, an oral airway may be used instead. In any event, the sound waves then travel through the trachea and lungs and impinge on the chest wall of the patient 12. The microphone 22 is responsive to the input sound waves generated by the speaker 20 and generates electrical signals representative of these input sound waves that are coupled to the amplifiers 30. In a similar manner, the surface sensors 24 and 26 are responsive to the vibrations imparted to the chest wall of the patient 12 by the sound waves and generate electrical signals representative of these chest wall vibrations that are coupled to the amplifiers 30. The electrical signals representative of the input sound waves and the chest wall vibrations are amplified by the amplifiers 30 and these amplified signals are coupled to the processing unit 34 which, as described in greater detail below, processes the amplified signals to enable a user to detect a respiratory condition within the patient 12.

The amplified signals associated with the input sound waves and the chest wall vibrations are converted into respective streams of digital data by the A/D 40 and these digital data streams are converted by the processor 38 into respective frequency domain representations (i.e., spectra) using a fast Fourier transform (FFT) or any other data processing technique that produces spectral data from digitized time domain waveforms. The spectrum associated with the input sound waves and the spectra associated with the chest wall vibrations can then be used to determine the transfer function of the patient's mouth, trachea, lungs and chest which, as described below, may include indicators of an abnormal respiratory condition within the patient 12. Additionally, the time domain waveforms associated with the input sound waves and the chest wall vibrations can be compared to one another to measure coherence and time delays between the input sound waves and the chest wall vibrations, which may also include indicators of an abnormal respiratory condition. Although two surface sensors are shown in the system 10 of FIG. 1, it is important to recognize that one, or any other number of surface sensors may be used instead to carry out the diagnostic techniques described herein without departing from the scope and the spirit of the invention.

FIGS. 2a–2f are exemplary graphical representations of the acoustic response characteristics of six test subjects (i.e., transfer functions) measured from their mouths to their chest walls using the system shown in FIG. 1. The solid lines shown in these graphs represent the acoustic response characteristics for a normal respiratory condition within each of the test subjects and the dashed lines represent the acoustic response characteristics for a pneumothorax condition within each of the test subjects. As can be seen in these graphs, the pneumothorax condition is characterized by a substantial attenuation of the sound waves having a frequency greater than about 300 Hz. In contrast, the sound waves having a frequency in the range of about 0 Hz to 250 Hz appear to be relatively unaffected by the pneumothorax condition.

Figure 3:
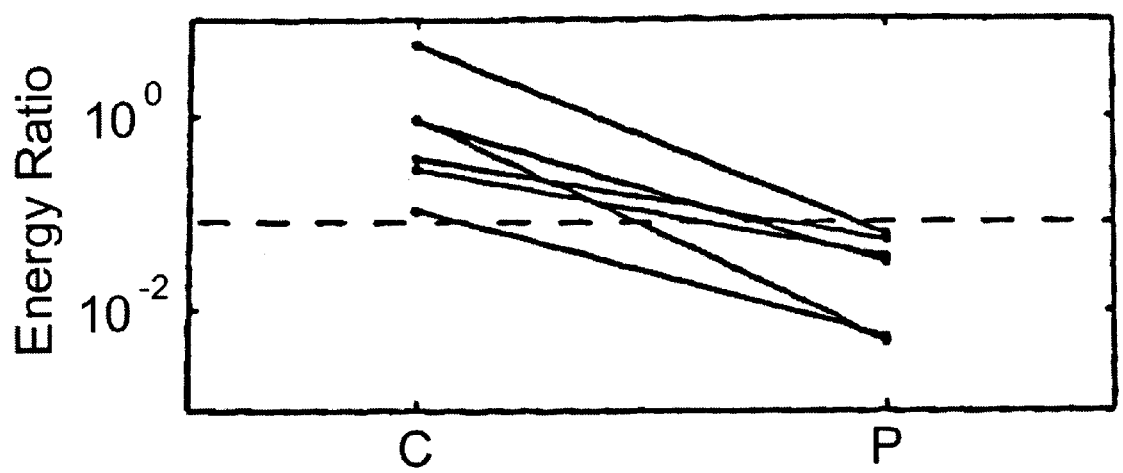
FIG. 3 is an exemplary graphical representation showing the ratios between the acoustic energies of a high frequency band of sound waves and a low frequency band of sound waves transmitted from the mouth to the chest wall within each of six test subjects using the system shown in FIG. 1.

FIG. 3 is an exemplary graphical representation showing the ratios between the acoustic energies of a high frequency band of sound waves and a low frequency band of sound waves transmitted from the mouth to the chest wall within each of six test subjects. For the measurements shown in FIG. 3, the high frequency band was defined as 550 Hz–780 Hz and the low frequency band was defined as 8 Hz–224 Hz. According to the test results shown in FIG. 2, the energy ratio (i.e., the energy associated with the high frequency band divided by the energy associated with low frequency band) decreases substantially when a pneumothorax condition is present. FIG. 3 shows the energy ratios calculated for both normal respiratory conditions, which are denoted as "C" on the horizontal axis, and pneumothorax conditions, which are denoted as "P" on the horizontal axis. As can be seen in FIG. 3, the energy ratio in all cases exceeded 0.10 for normal respiratory conditions and, in all cases, fell below 0.06 for abnormal respiratory conditions due to pneumothorax. Thus, a threshold value of 0.08 completely separates a normal respiratory condition from an abnormal pneumothorax state so that if an energy ratio of less than 0.08 is calculated by the system 10, the system 10 can reasonably indicate to the user (e.g., a physician) that a pneumothorax condition is probably present.

Figure 4:
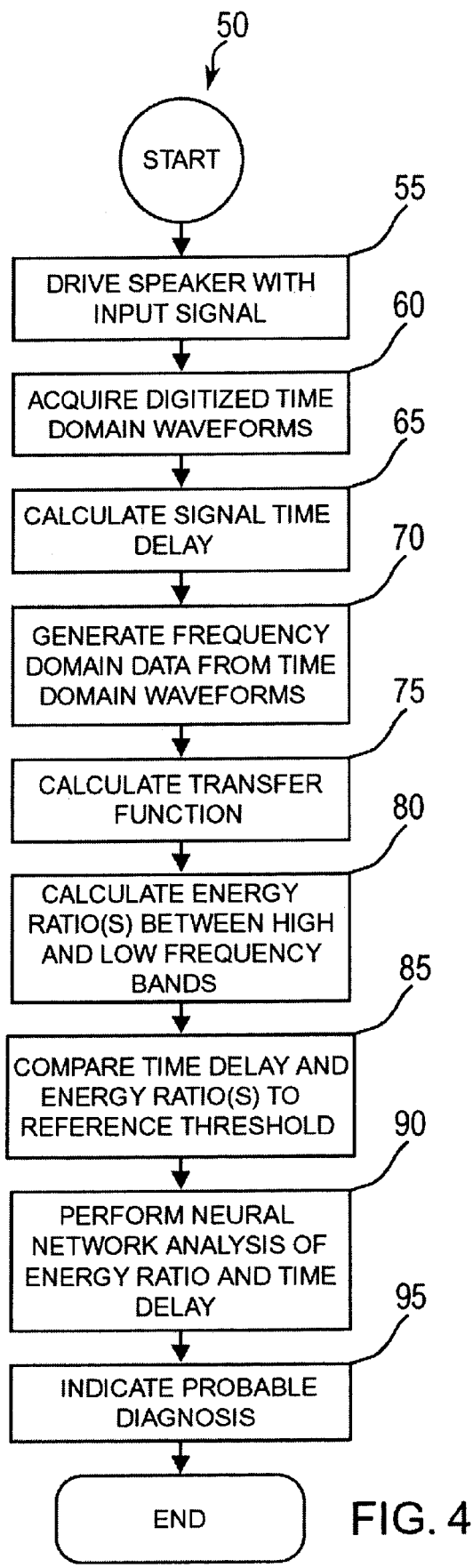
FIG. 4 is a flow diagram representing one method by which the acoustic response characteristics of a patient's chest and lungs may be analyzed using the system shown in FIG. 1.

FIG. 4 is a flow diagram representing one method 50 by which the acoustic response characteristics of a patient's chest and lungs may be analyzed using the system shown in FIG. 1. In a first block 55, the processing unit 34 sends input signals to the signal conditioning unit 28 that are amplified by the output driver 32 and coupled to the speaker 20. Preferably, but not necessarily, these amplified input signals cause the speaker 20 to produce sound waves having a broadband noise characteristic. For example, the speaker 20 may generate sound waves having a relatively constant amplitude over a frequency range of 20 Hz to 1600 Hz. Of course, other frequency ranges and amplitude characteristics could be used as well without departing from the scope of the invention. For example, a click signal, a chirp signal, swept frequency signal or a signal containing a single frequency or a selected band of frequencies could be used instead of a broadband noise signal.

In block 60, the processing unit 34 acquires digitized time domain waveforms associated with inputs received from the microphone 22 and one or more of the surface sensors 24 and 26. As will be discussed in greater detail below, depending on the particular respiratory condition that the user desires to detect, the signals from one or more of the surface sensors 24 and 26 maybe acquired by the processing unit 34. Additionally, the precise location of the surface sensors 24 and 26 on the chest of the patient 12 may be varied to optimize detection of a particular respiratory condition. For example, to detect a pneumothorax condition, the surface sensors 24 and 26 may be located at the clavicle lines at about the level of the third rib (on the left and right sides) of the patient 12. Further, in block 60, the processing unit 34 stores the digitized waveforms in the memory 36 for subsequent processing.

In block 65, the processing unit 34 calculates an input signal transmission time delay by comparing the acquired time domain signal associated with the microphone 22 to the acquired time domain signals associated with the surface sensors 24 and 26. The transmission time delay represents the amount of time it takes for sound waves to travel from the mouth of the patient 12 to the locations on the chest wall of the patient 12 that are adjacent to the surface sensors 24 and 26.

In block 70, the processing unit 34 generates frequency domain data from the acquired time domain signals. In other words, the processing unit 34 generates spectra representative of the input sound waves and chest wall vibrations. In block 75, the processing unit 34 uses the spectral data generated in block 70 to calculate the transfer function from the patient's mouth to the chest wall as the quotient of the cross spectrum of the input sound waves and the chest wall vibrations and the power spectrum of the input sound waves.

In block 80, the processing unit 34 calculates an energy ratio (or ratios if signals from both of the surface sensors 24 and 26 are used) by determining the total acoustic energy in a high frequency band, which may, for example, be 550

Hz–780 Hz, and the total acoustic energy in a low frequency band, which may, for example, be 8 Hz–224 Hz, and then dividing the total energy for the high frequency band by the total energy calculated for the low frequency band. These total energy calculations may, for example, be made by adding the transfer function values for all of the frequency bins (i.e., the discrete frequencies associated with FFT results) within each frequency band. Further, the spectral ranges associated with the upper and lower frequency bands may be optimized to enable the detection of particular respiratory conditions.

In block 85, the processing unit 34 compares the time delay calculated in block 65 to a predetermined time delay threshold value and compares the energy ratios calculated in block 80 to a predetermined energy ratio threshold, which may, for example, be 0.08 as discussed above. In block 90, the processing unit 34 performs a neural network analysis of the time delay value from block 65 and the energy ratio value from block 80. As is commonly known, neural networks are essentially one or more software routines that are responsive to input parameters based on a set of training data, which condition the behavior of the network. For example, a set of training data containing energy ratios and time delay values associated with known respiratory conditions could be used to train the neural network routines. The neural network routines may, for example, generate a diagnostic indicator value, which may range from zero to one and which is indicative of a possible diagnosis. The value "1" may represent a healthy patient and the value "0" may represent a particular abnormal respiratory condition, and values between zero and one may represent the degree to which a patient's condition corresponds to either the healthy condition or the abnormal respiratory condition. In operation, the trained neural network routines receive calculated time delay values and energy ratio values and use these values to generate a diagnostic indicator value ranging from zero to one.

In block 95, the processing unit 34 may use one or more of the comparisons of the time delays and the energy ratios to the respective time delay and/or energy ratio thresholds and/or may also use the output of the neural network analysis (i.e., the diagnostic indicator), or any other suitable output classification scheme, to indicate a probable diagnosis to the user. For example, if the result of the comparison of the energy ratio to the energy ratio reference threshold in block 85 is that the energy ratio exceeds the energy ratio reference threshold and/or, if the time delay falls outside of an allowable range of time delays, the processing unit 34 may indicate (via a textual and/or graphical display within the display 46) in block 95 that an abnormal respiratory condition, such as pneumothorax, is present. Alternatively or additionally, if the neural network analysis in block 90 produces a diagnostic indicator value which is sufficiently close to zero (or at least is below some threshold associated with a normal healthy condition), then the processing unit 34 in block 95 may indicate that an abnormal respiratory condition, such as pneumothorax, is present. Still further, the probable diagnosis determined in block 95 may be a result of any combination of comparisons made in block 85 and the neural network analysis of block 90. In fact, it may be desirable in some applications to require use of more than one of these comparisons and/or the neural network analysis to achieve a higher confidence in the probable diagnosis determined in block 95.

Figure 5:
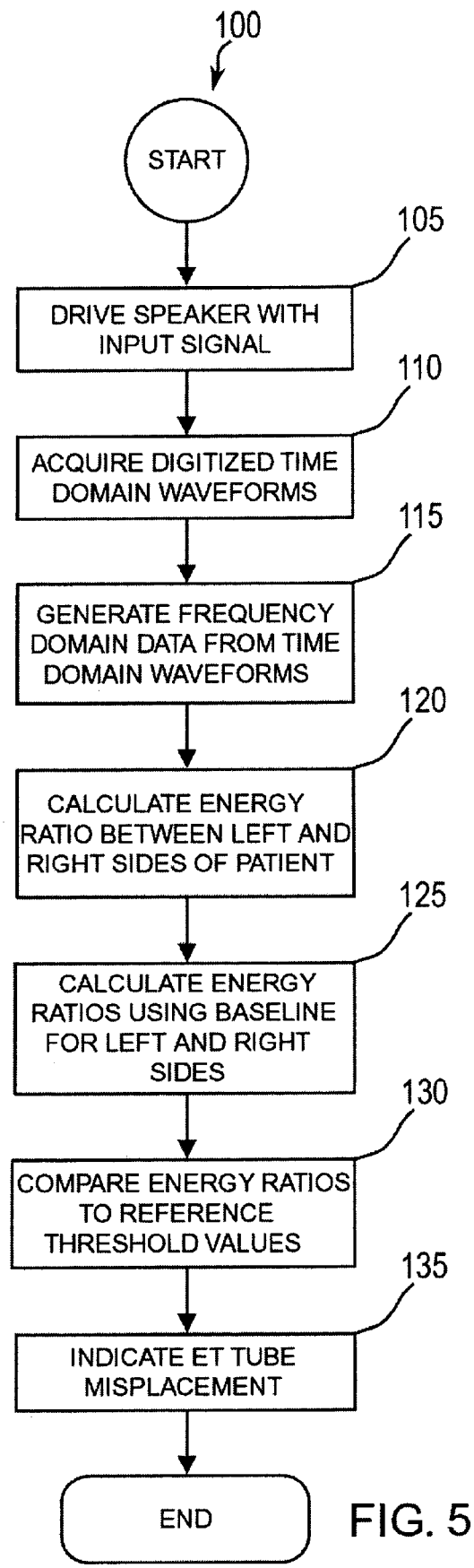
FIG. 5 is a flow diagram representing another method by which the acoustic response characteristics of a patient's chest and lungs may be measured using the system shown in FIG. 1.

FIG. 5 is a flow diagram representing another method 100 by which the acoustic response characteristics of a patient's chest and lungs may be measured using the system of FIG. 1. As discussed in greater detail below, the method 100 may be used to determine whether an ET tube has been properly located within a patient's trachea. More specifically, the method 100 enables a user (e.g., a physician) to determine on a real time basis whether an ET tube has been misplaced such that the one of the patient's bronchi is partially or completely blocked, thereby creating an abnormal respiratory condition within the patient 12 (FIG. 1). Typically, to detect ET tube placement, the surface sensors 24 and 26 are located so that one of the surface sensors 24 and 26 is adjacent to the left side of the patient's chest and the other sensor is located adjacent to the right side of the patient's chest.

In block 105, the processing unit 34 (FIG. 1) sends input signals to the signal conditioning unit 28 that cause the speaker 20 to produce sound waves having a broadband noise characteristic and, in block 110, the processing unit 34 acquires digitized time domain waveforms associated with inputs received from one or more of the surface sensors 24 and 26. To detect an abnormal respiratory condition such as an ET tube misplacement within a patient's trachea, the time domain waveforms acquired in block 110 may be acquired multiple times. For example, time domain waveforms may be acquired before the ET tube 14 has been inserted into the patient 12 to establish baseline acoustic characteristics. Additional time domain waveforms may then be acquired repeatedly as the ET tube 14 is inserted and, as described in greater detail below, the acoustic characteristics derived from these additional time domain waveforms may be compared to one another and to the initial baseline characteristics to determine whether the ET tube 14 is positioned improperly.

In block 115, the processing unit 34 generates frequency domain data (i.e.,.spectral data) from each of the time domain waveforms acquired in block 110 and stores this frequency data in the memory 36. In block 120, the processing unit 34 calculates an energy ratio between the left and right sides of the patient 12 by dividing the total energy within a frequency band of the frequency domain data associated with one of the surface sensors 24 and 26 by the total energy within a corresponding frequency band of the frequency domain data associated with the other one of the surface sensors 24 and 26. Thus, in block 120, the processing unit 34 calculates a value that is indicative of a relative comparison between the intensity of the vibrations or sound waves received by the surface sensors 24 and 26 within a particular frequency band.

While the method 100 of FIG. 5 is described by way of example to use a single frequency band to calculate energy ratios, additional frequency bands could alternatively be used to calculate the one or more energy ratios without departing from the scope of the invention.

In block 125, the processing unit 34 calculates energy ratios by dividing the energies within a particular frequency band (or bands) by respective baseline energies within that band (or bands) that are established prior to insertion of the ET tube 14. In block 130, the processing unit 34 compares the energy ratios calculated in blocks 120 and 125 to a set of reference threshold values and, in block 135, the processing unit uses the results of the comparisons made in block 130 to indicate whether or not the ET tube 14 is properly positioned within the patient's trachea. When an ET tube is misplaced, it typically migrates into one of the main bronchi, which results in sound waves being attenuated more on the side associated with the obstructed bronchus as compared to the other (i.e., unobstructed) side of the patient 12 and also results in the sound waves or vibrations measured on the obstructed side being attenuated with respect to the baseline measurements of that side. In block 135, the processing unit 34 indicates that the ET tube 14 has been misplaced (i.e., has migrated into one of the main bronchi) when the energy ratio between the left and right side measurements crosses a predetermined threshold value, which may be adjusted by the user to control the sensitivity of the system 10. Alternatively or additionally, the processing unit 34 may use the results of the comparisons of the energy ratios based on the left and right side measurements and the respective baseline left and right side measurements to determine whether the ET tube 14 has been misplaced.

The system 10 shown in FIG. 1 may also be used to detect respiratory conditions without using any input of sound waves to the patient's mouth and trachea. Instead, one or more of the surface sensors 24 and 26 may be used to analyze indigenous respiratory sounds to assess the respiratory conditions within the patient 12.

Respiratory sounds are routinely used for clinical assessment of respiratory function and the characteristics of normal and some abnormal respiratory sounds have been extensively studied. The normal respiratory sound spectrum is known to peak below 100 Hz where the signal is mixed with muscle and cardiovascular sounds. Above 100 Hz, the signal amplitude drops sharply but is still measurable up to about 1000 Hz [Pasterkamp et al. 96]. Higher frequencies are more pronounced in smaller subjects, which is usually attributed to less transmission attenuation in their smaller lungs and thinner chest walls. The sound amplitude is known to be proportional to the square of the airflow, to increase toward the lung bases posteriorly and to decrease toward the bases anteriorly. These sounds depend on respiratory cycle timing because of intra-cyclic airflow variability. Furthermore, the reversal in airflow directionality during inspiration compared to expiration alters sound generation in different lung regions secondary to flow turbulence changes.

As is commonly known, pneumothorax results in diminished breath sounds during physical examination. Other conditions that can lead to faint lung sounds include stenosis of the main, intermediate, or lobar bronchi, which can be detected over the parts of the lung supplied by the affected airway, whereas vocalizations tend to be unchanged at these locations. Some studies have also correlated poor ventilation with diminished lung sounds in the frequency below 300 Hz, which may overlap with the pneumothorax acoustic signature.

FIGS. 6a–6f are exemplary graphical representations showing spectra of indigenous respiratory sounds for normal and pneumothorax states within six test subjects. Each spectrum shown in FIGS. 6a–6f contains more than twelve respiratory cycles for each of the six test subjects. Using a FFT, the spectral content of the respiratory sounds was calculated for each 1024-point data segment after windowing with a Hanning window, which resulted in a frequency resolution of 8 Hz. Data segments overlapped by 50% and the mean spectral values were determined by averaging results from all segments. Tracking the respiratory cycle with a separate sensor, or with a contact sensor as described above, enables respiratory sound analysis at different points within the respiratory cycle. This type of gated analysis helps to optimize the performance of the system 10.

As shown in FIGS. 6a–6f, at frequencies below 30 Hz the amplitude of respiratory sounds within each test subject decreases with decreasing frequency due to the inherent high pass cut off (at 20 Hz) of the electronic stethoscopes used for the surface sensors 24 and 26. Signal amplitudes of the normal respiratory condition and the abnormal pneumothorax condition were not significantly different below 100 Hz–200 Hz. In fact, the amplitude attenuated at 21.8+−2.9 dB/Octave (mean+−standard deviation) with increasing frequency in the 30 Hz–200 Hz range under both normal respiratory conditions and abnormal respiratory conditions. This drop in amplitude may be due to an increase in sound transmission resistance and a decrease in sound generation.

Amplitude changes as a result of pneumothorax were most pronounced in the 300 Hz to 500 Hz range. This difference likely results from the large impedance mismatch that occurs when the lung pulls away from the inner chest wall forming an air gap or gas cavity and also results from decreased sound generation in the respiratory system as a result of decreased airflow and turbulence.

In any event, as suggested by the spectral graphs shown in FIGS. 6a–6f, the method 50 shown in FIG. 4 may be used to analyze indigenous respiratory sounds to detect abnormal respiratory conditions. However, in using the method 50 of FIG. 4, the block 55, which drives the speaker 20 to cause sound waves to enter the patient's mouth, is omitted, and any signal time delay calculations or use of time delay values are similarly omitted. Additionally, in adapting the method 50 of FIG. 4 for use in analyzing indigenous respiratory sounds, the frequency bands used to calculate the energy ratios may be optimized to maximize the confidence in the diagnostic output in block 95.

Because respiratory sounds are primarily a result of airflow-induced turbulence, the method 100 shown in FIG. 5 (less block 105) may also be used to analyze indigenous respiratory sounds to detect an abnormal respiratory condition such as a misplaced ET tube. When the ET tube is misplaced, ventilation is reduced in one of the lungs, which results in a decrease in the intensity of the respiratory sounds detected at the chest surface adjacent to the obstructed lung. In addition, the increase in airflow to the unobstructed lung causes an increase in the intensity of the respiratory sounds at the chest surface adjacent to the unobstructed lung, which further increases the sensitivity of the system 10 to a misplaced ET tube.

Further, because attenuation of acoustic waves within the respiratory system typically increases with frequency (i.e., higher frequencies are more heavily damped), the higher frequency components of indigenous respiratory sounds are more easily detected close to their point of origin. Thus, if an ET tube is misplaced and extends into the one of the main bronchi, then the intensity of the high frequency components of the indigenous respiratory sounds generated by the under ventilated (i.e., obstructed) lung will decrease.

Figure 7B:
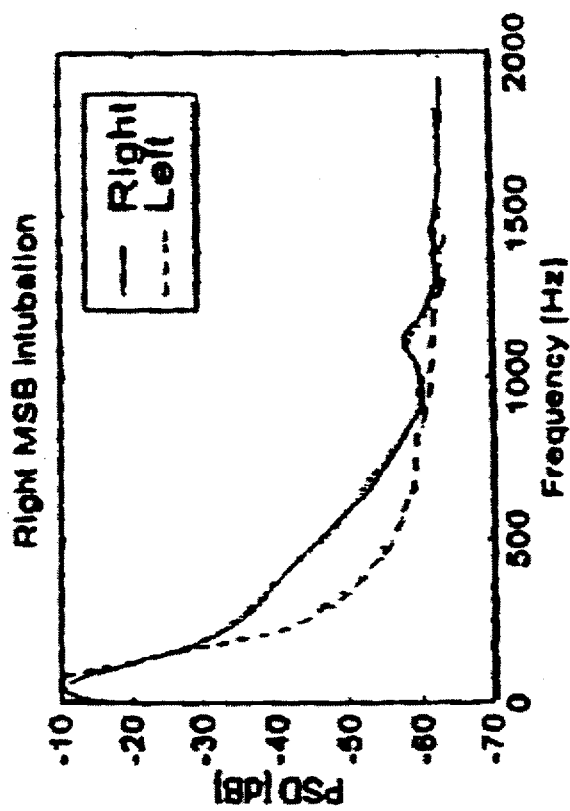
Figure 7A:
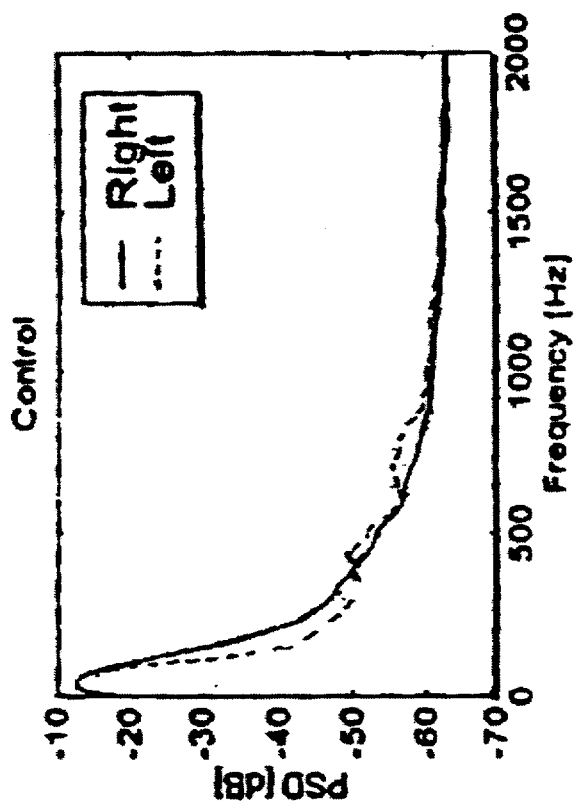
FIG. 7a is an exemplary graphical representation showing spectra of indigenous respiratory sounds for a normal respiratory condition within a typical test subject.

FIG. 7a is an exemplary graphical representation showing spectra of indigenous respiratory sounds for a normal respiratory condition within a typical test subject, and FIG. 7b is an exemplary graphical representation showing spectra of indigenous respiratory sounds for an abnormal respiratory condition in which an ET tube has migrated into the right bronchus of the test subject of FIG. 7a. As can be seen in FIGS. 7a and 7b, there is a general trend for increased attenuation with increasing frequency over the 50 Hz to 1500 Hz range. However, as shown in FIG. 7b, the over-advancement of the ET tube into the right bronchus results in a significant attenuation in the intensity of indigenous respiratory sounds within the left lung over the 200 Hz to 1200 Hz range. A maximum attenuation of indigenous respiratory sounds of about 15–20 dB was observed at about 400 Hz in the left lung.

Still further, if the ET tube is misplaced into the esophagus, ventilator air is forced into the stomach, which results in relatively loud epigastric sounds. Due to the substantial anatomic differences between the respiratory and upper gastrointestinal systems, sounds resulting from esophageal ventilation have spectral and temporal characteristics that are substantially different from normal condition respiratory sounds. For example, ventilation of the upper gastrointestinal tract exhibits a minimal expiratory phase, at least until enough air accumulates to cause a significant back pressure.

Still further, acoustic changes resulting from extubation depend primarily on the new ET tube position. Typically, pharyngeal positioning of the ET tube generates some transmitted acoustic energy to the chest wall. However, attenuation of higher frequencies and the amplitude of bilateral respiratory sounds also occurs.

Figure 8:
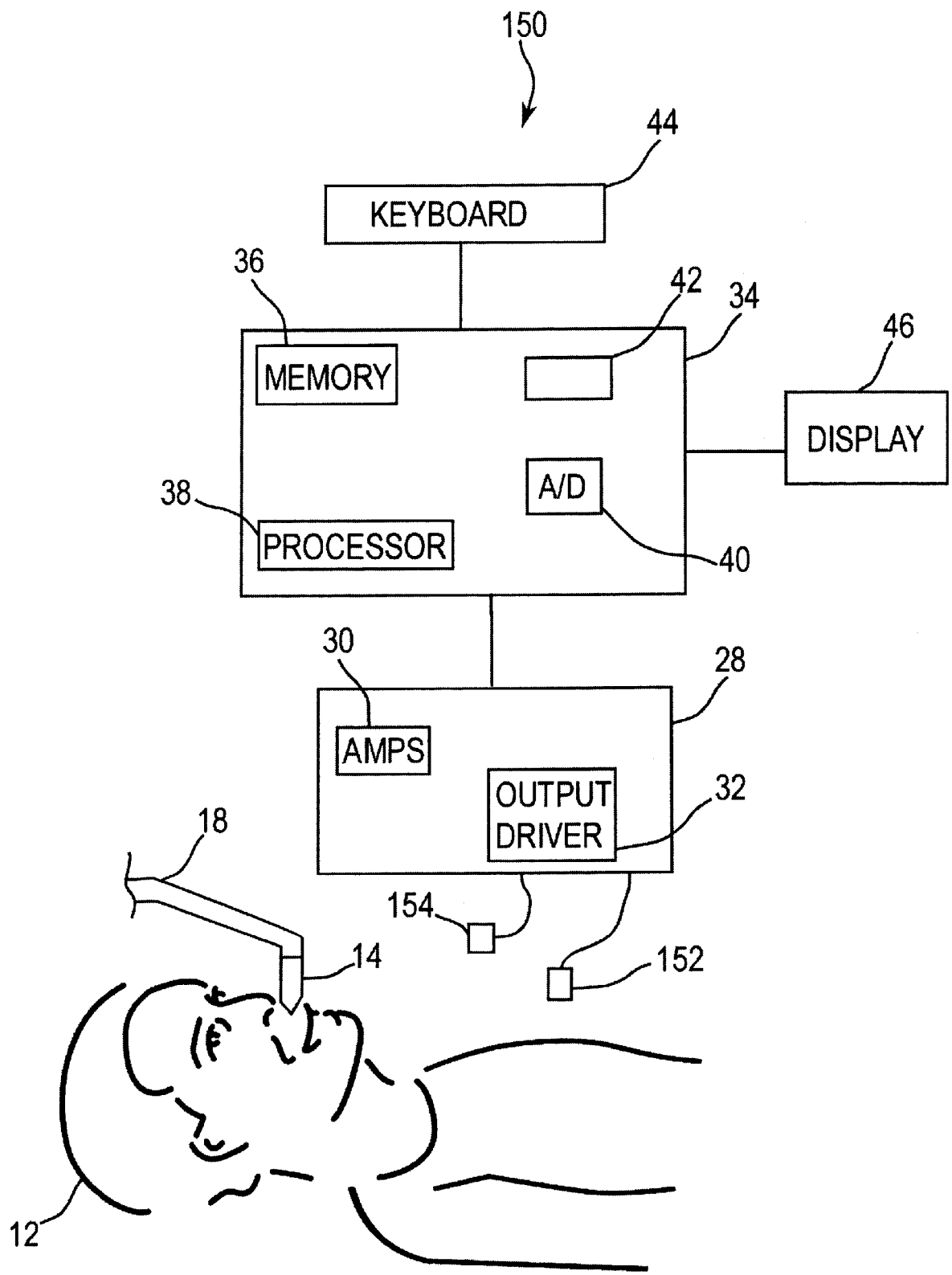
FIG. 8 is an exemplary schematic block diagram of an alternative system that uses percussive inputs to measure the acoustic response characteristics within the chest and lungs of an endotracheally intubated patient.

FIG. 8 is an exemplary schematic block diagram of an alternative system 150 that uses percussive inputs to measure the acoustic response characteristics of an endotracheally intubated patient's chest and lungs. Elements of the system 150 that are similar or the same as those of the system 10 shown in FIG. 1 are identified using the same reference numerals. However, in the alternative system 150 of FIG. 8, an impact hammer 152 and an air-coupled microphone 154 have been added to enable the detection of respiratory conditions within the patient 12 using percussive inputs to the patient's chest.

The alternative system 150 uses the impact hammer 152 to apply percussive inputs to the chest of the patient 12. The impact hammer 152 may be any suitable actuation device that imparts vibrations to the chest of the patient 12. Further, the hammer 152 may be manually activated by a user (e.g., a physician, technician, etc.) or may be activated automatically in the case where the hammer 152 is electrically powered such as, for example, where the hammer 152 is actuated by a solenoid. The hammer 152 may contact the chest of the patient 12 directly or, alternatively, may impact an anvil that interposes between the chest surface and the hammer 152.

The air-coupled microphone 154 is responsive to the sounds that emanate from the patient's chest following a percussive input by the hammer 152 and sends electrical signals representative of these sounds to the signal conditioning unit 28. The signal conditioning unit 28 uses the amplifiers 30 to amplify these electrical signals and couples the amplified signals to the processing unit 34 for further processing.

Figure 9:
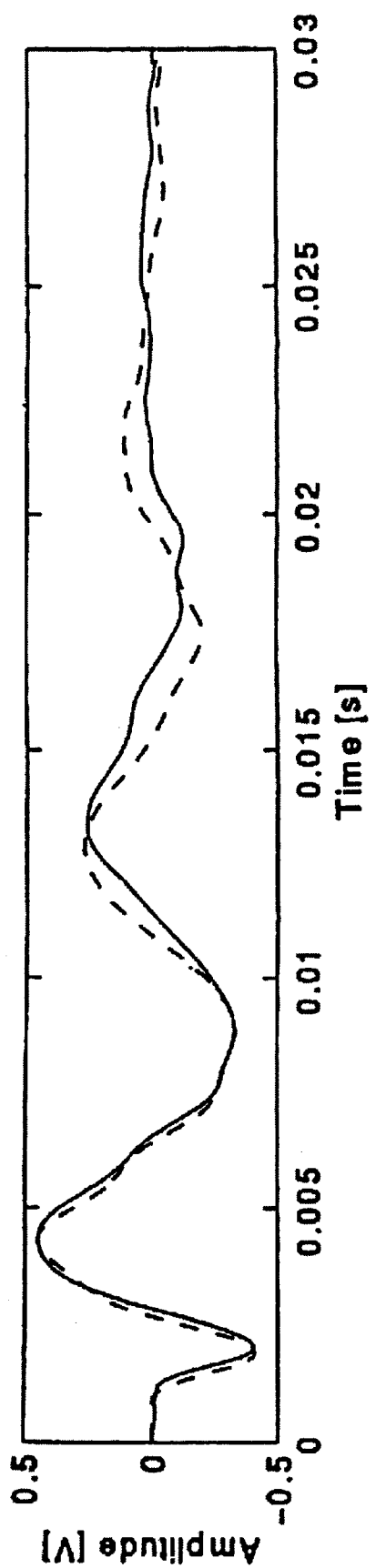
FIG. 9 is an exemplary graphical representation showing a typical acoustic chest response to a percussive input for a normal respiratory condition and a pneumothorax condition.

FIG. 9 is an exemplary graphical representation showing a typical acoustic chest response to a percussive input for a normal respiratory condition (solid line) and a pneumothorax condition (dashed line). In developing the graph shown in FIG. 9, percussion was introduced in seven dogs at the right mid-clavicular line by activating the impact hammer 152 to cause it to strike a stainless steel circular bar held against the chest wall parallel to the ribs in the third intercostal space. Percussion tests were performed for both normal respiratory conditions and a pneumothorax condition. During each test, fifteen percussive inputs were performed and the chest response was measured using the air-coupled microphone 154 placed a small distance away from the skin. The amplitude, dominant frequency, and decay rate were calculated for each input.

As shown in FIG. 9, each of the signals representative of the normal and pneumothorax conditions are about 20–30 ms in duration and show an initial spike followed by a decaying oscillatory signal with a narrow-band spectral content, which is typical of underdamped vibrating systems. However, it is clear from the percussive test results that the damped oscillatory response associated with a pneumothorax condition has a slower decay rate and also has a higher frequency than that of a normal respiratory condition.

The slower decay rate and the higher frequency associated with a pneumothorax condition may be a result of the tendency of the chest wall to vibrate at its natural frequency in response to percussive inputs and the fact that vibrations decay in time as a result of viscous dissipation of vibratory mechanical energy in the chest wall and lungs. Specifically, when pneumothorax is present, the lung pulls away from the chest wall and produces less damping, which results in a lower decay rate. In addition, as the underlying parenchyma is replaced by air, the vibrating mass of the system is lowered, which increases the resonant frequency of the system. These effects are consistent with what has been noted by skilled physicians as "hyperresonance" during physical examination.

Quantitative analysis of the above-noted percussive signals was performed to determine their decay rate and dominant frequency. To calculate the decay rate, the signal envelope was first determined as the instantaneous amplitude of the signal, followed by finding the best fit of the decaying portion of the envelope using regression analysis. The slope of the fitted curve then gave the decay rate. Both linear and exponential decay calculations were attempted. The dominant frequency was estimated from both zero-crossing and FFT algorithms. Zero-crossing provided a finer resolution (1–5 Hz in the 80–200 Hz range) as the FFT estimate was limited to 40 Hz due to the short duration of the signals. Wavelets and autoregressive analysis including the maximum entropy method were also performed.

Because of the large intersubject variability suggested by the data, parameter values of the control state (e.g., from the contralateral side or an initial baseline value at the same side) may be needed for accurate diagnosis. The large intersubject variability may be the reason for the conflicting reports about the sensitivity and specificity of manual percussion for the diagnosis of lung diseases.

Figure 10:
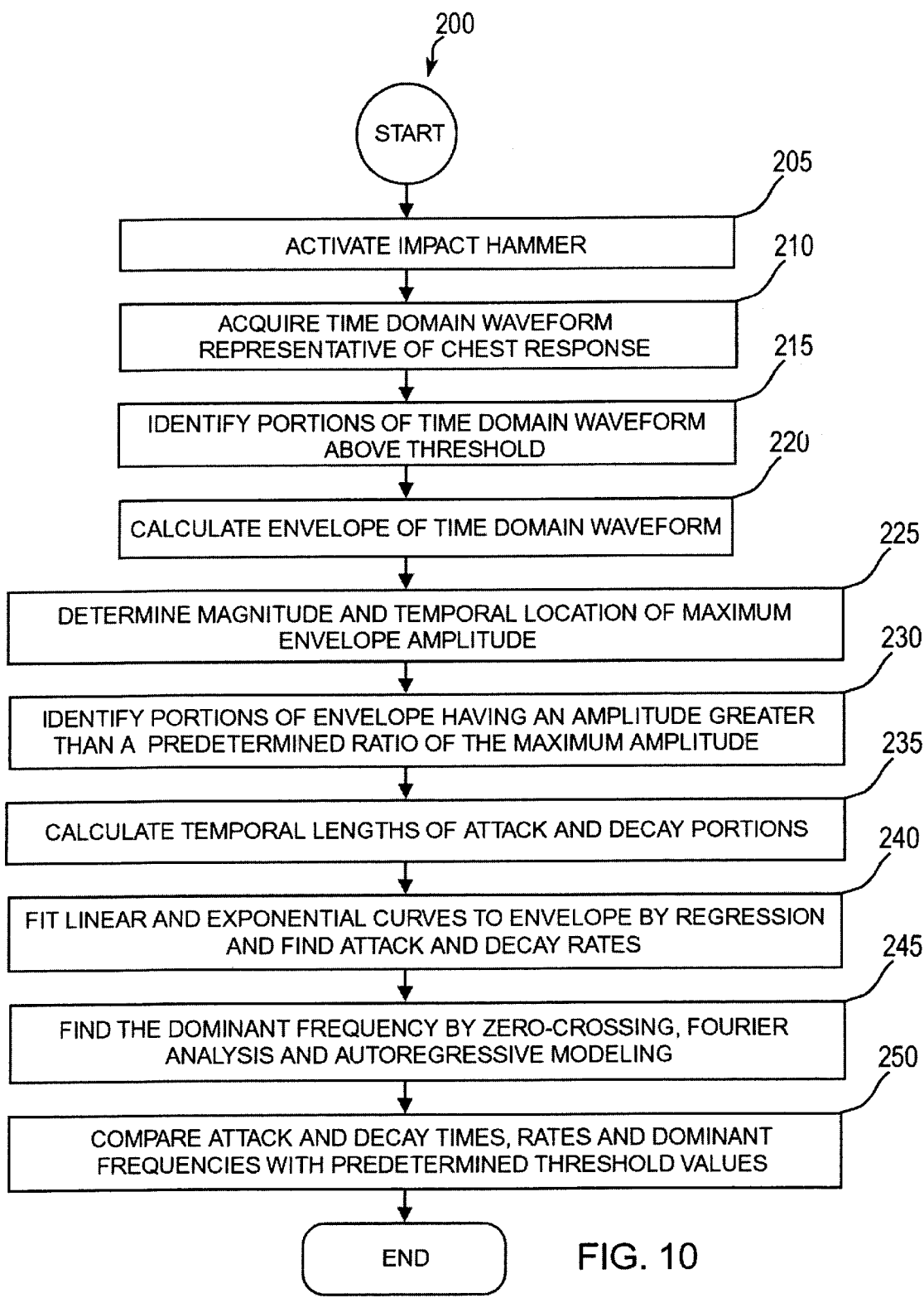
FIG. 10 is a flow diagram representing one method by which the acoustic response characteristics of a patient's chest and lungs may be analyzed using the system shown in FIG. 8.

FIG. 10 is a flow diagram representing one method 200 by which the acoustic response characteristics of a patient's chest and lungs can be analyzed using the system 150 shown in FIG. 8. In block 205, the processing unit 34 activates the impact hammer 152 to impact the chest of the patient 12 and, in block 210, the processing unit 34 receives electrical signals via the microphone 154 and the amplifiers 30 that are representative of vibrations resulting in the patient's chest from the impact of the hammer 152. In block 215, the processing unit 34 monitors the acquired time domain waveform and identifies portions of the time domain waveform that are above a predetermined threshold for subsequent processing. Those portions of the waveform that fall below the predetermined threshold are not processed any further and are considered to be spurious and/or noise-related.

In block 220, the processing unit 34 calculates the envelope of the portions of the time domain waveform identified as above the threshold in block 215. By way of example only, a Hilbert transform or any other envelope calculation technique may be used to calculate the envelope of the time domain waveform. In block 225, the processing unit 34 determines the temporal location and the magnitude of the maximum envelope amplitude and, in block 230, the processing unit 34 identifies portions of the envelope (surrounding the location of the maximum amplitude) having an amplitude greater than a predetermined ratio of the maximum amplitude. For example, the predetermined ratio may be set to 20% so that the portions of the envelope identified in block 230 extend temporally to either side of the maximum envelope value to the points where the envelope amplitude is 20% of the maximum envelope amplitude.

In block 235, the processing unit 34 calculates the temporal lengths of the attack portion of the envelope, which is the identified portion preceding the temporal location of the maximum envelope value, and the decay portion, which corresponds to the identified portion that follows the temporal location of the maximum envelope value. In block 240, the processing unit 34 fits the attack and decay portions of the envelope to linear and/or exponential curves by regression and then uses the results of the regression (i.e., the curve fit) to calculate the attack and decay rates (i.e., the slopes of the fit curves).

In block 245, the processing unit 34 determines the dominant frequency using zero-crossing, Fourier analysis and autoregressive modeling, which are all well known techniques for determining the frequency of a time domain signal. In block 250, the processing unit 34 compares the attack and decay times, attack and decay rates and dominant frequencies with predetermined threshold values. For example, if the dominant frequency is found to be greater than a dominant frequency threshold value associated with an abnormal respiratory condition such as pneumothorax, then the processing unit 34 may send indications to the user via the display 46 that a pneumothorax condition is probably present. Similar comparisons of the decay times and rates to predetermined threshold values associated with one or more different respiratory conditions can be made that result in the indication of a probable diagnosis to the user. Further, the attack and decay times, as well as the dominant frequencies, can be passed through a neural network analysis (similar to that discussed above in connection with FIG. 4) to provide increased confidence in the diagnostic outputs that are presented to the user.

If implemented in software, the functional blocks and routines discussed herein may be stored in any computer readable memory such as on a magnetic, an optical, or other storage medium, in a RAM or ROM of a computer, controller, field device, etc. Likewise, this software may be modulated on a carrier and delivered to a user or a device via any known or desired delivery method including, for example, over a communication channel such as a telephone line, the Internet, etc.

While the invention has been described with reference to specific examples, which are intended to be illustrative only and not to be limiting of the invention, it will be apparent to those of ordinary skill in the art that changes, additions or deletions may be made to the disclosed embodiments without departing from the spirit and the scope of the invention.

What is claimed is:

1. A method of detecting a respiratory condition within a body, the method comprising the steps of:

emitting sound waves into an opening of the body;

receiving the emitted sound waves;

converting the emitted sound waves into a first electrical signal;

receiving vibrations resulting from the sound waves interacting with the respiratory condition and impinging on a location of the body;

converting the received vibrations into a second electrical signal; and using the first and second electrical signals to calculate a value indicative of the respiratory condition.

2. The method of claim 1, wherein the step of using the first and second electrical signals to calculate the value indicative of the respiratory condition includes the steps of:

generating a first set of frequency data using the first electrical signal;

generating a second set of frequency data using the second electrical signal;

calculating transfer function data using the first and second sets of frequency data; and using the transfer function data to calculate an energy ratio indicative of the respiratory condition.

3. The method of claim 2, wherein the step of using the transfer function data to calculate the energy ratio indicative of the respiratory condition includes the step of calculating the energy ratio indicative of the respiratory condition based on a first energy within a first band of frequencies and a second energy within a second band of frequencies.

4. The method of claim 3, wherein the step of calculating the energy ratio based on the first energy within the first band of frequencies and the second energy within the second band of frequencies includes the step of defining the first band of frequencies to include higher frequency components than the second band of frequencies.

5. The method of claim 2, wherein the steps of generating the first and second sets of frequency data include the step of using a fast Fourier transform.

6. The method of claim 1, wherein the step of receiving the vibrations resulting from the sound waves interacting with the respiratory condition and impinging on the location of the body includes the step of receiving the vibrations adjacent to a surface of the body.

7. The method of claim 6, wherein the step of receiving the vibrations adjacent to the surface of the body includes the step of receiving the vibrations adjacent to a chest wall of the body.

8. The method of claim 1, wherein the step of emitting the sound waves into the opening of the body includes the step of emitting broadband noise into the opening of the body.

9. The method of claim 1, wherein the step of emitting the sound waves into the opening of the body includes the step of emitting the sound waves into a mouth portion of the body.

10. The method of claim 2, further comprising the steps of comparing the energy ratio indicative of the respiratory condition to a reference threshold and generating an output indicative of the comparison.

11. The method of claim 10, wherein the step of providing the output indicative of the comparison includes the step of generating an output indicative of a pneumothorax condition.

12. The method of claim 10, wherein the step of providing the output indicative of the comparison includes the step of generating an output indicative of a misplaced endotracheal tube.

13. The method of claim 2, further comprising the steps of using the first and second electrical signals to calculate a time delay and using a neural network to process the time delay and the energy ratio to generate an output indicative of the respiratory condition.

14. The method of claim 13, wherein the step of using the neural network to process the time delay and the energy ratio to generate the output indicative of the respiratory condition includes the step of generating an output indicative of a pneumothorax condition.

15. The method of claim 13, wherein the step of using the neural network to process the time delay and the energy ratio to generate the output indicative of the respiratory condition includes the step of generating an output indicative of a misplaced endotracheal tube.

16. The method of claim 1, wherein the step of using the first and second electrical signals to calculate the value indicative of the respiratory condition includes the steps of calculating a signal time delay between the first and second electrical signals and comparing the signal time delay to a predetermined threshold value.

17. The method of claim 16, wherein the step of comparing the signal time delay to the predetermined threshold value includes the step of using a predetermined threshold value associated with a pneumothorax condition.

18. The method of claim 16, wherein the step of comparing the signal time delay to the predetermined threshold value includes the step of using a predetermined threshold value associated with a misplaced endotracheal tube.

19. A system for use in detecting a respiratory condition within a body, the system comprising:
 a source of sound waves that emits sound waves into an opening of the body;
 a first transducer that converts the sound waves emitted into the opening of the body into a first electrical signal;
 a second transducer adjacent to a location on the body that receives vibrations resulting from the sound waves interacting with the respiratory condition and impinging on the location on the body and converts the received vibrations into a second electrical signal; and
 a processing unit that uses the first and second electrical signals to calculate a value indicative of the respiratory condition.

20. The system of claim 19, wherein the first transducer is a microphone.

21. The system of claim 19, wherein the second transducer is a vibration sensor.

22. The system of claim 19, wherein the source of sound waves is a speaker.

23. The system of claim 19, wherein the respiratory condition is pneumothorax.

24. The system of claim 19, wherein the respiratory condition is a misplaced endotracheal tube.

25. The system of claim 19, wherein the processing unit:
 generates a first set of frequency data using the first electrical signal;
 generates a second set of frequency data using the second electrical signal;
 calculates transfer function data using the first and second sets of frequency data; and
 uses the transfer function data to calculate an energy ratio indicative of the respiratory condition.

26. The system of claim 25, wherein the processing unit calculates the energy ratio indicative of the respiratory condition based on a first energy within a first band of frequencies and a second energy within a second band of frequencies.

27. The system of claim 26, wherein the first band of frequencies includes higher frequency components than the second band of frequencies.

28. The system of claim 19, wherein the processing unit calculates a signal time delay between the first and second electrical signals and compares the signal time delay to a predetermined threshold value.

29. A system for use in an apparatus having a processor that emits sound waves into an opening of a body to detect a respiratory condition within the body, the system comprising:

a computer readable medium;
 a plurality of routines stored on the computer readable medium and adapted to be executed by the processor, wherein the plurality of routines comprises:
 a first routine that is adapted to convert the sound waves emitted into the opening of the body into a first electrical signal;
 a second routine that is adapted to convert vibrations resulting from the emitted sound waves interacting with the respiratory condition and impinging on a location of the body into a second electrical signal; and
 a third routine that is adapted to use the first and second electrical signals to calculate a value indicative of the respiratory condition.

30. The system of claim 29, wherein the third routine is further adapted to:
 generate a first set of frequency data using the first electrical signal;
 generate a second set of frequency data using the second electrical signal;
 calculate transfer function data using the first and second sets of frequency data; and
 use the transfer function data to calculate an energy ratio indicative of the respiratory condition.

31. The system of claim 30, wherein the third routine is further adapted to calculate the energy ratio based on a first energy within a first band of frequencies and a second energy within a second band of frequencies.

32. The system of claim 31, wherein the third routine is further adapted to define the first band of frequencies to include higher frequency components than the second band of frequencies.

33. The system of claim 30, wherein the plurality of routines further comprises a fourth routine that is adapted to compare the energy ratio indicative of the respiratory condition to a reference threshold and generate an output indicative of the comparison.

34. The system of claim 33, wherein the fourth routine is further adapted to generate an output indicative of a pneumothorax condition.

35. The system of claim 33, wherein the fourth routine is further adapted to generate an output indicative of a misplaced endotracheal tube.

36. The system of claim 30, wherein the plurality of routines further comprises a fourth routine that is adapted to use the first and second electrical signals to calculate a time delay and to use a neural network to process the time delay and the energy ratio indicative of the respiratory condition to generate an output indicative of the respiratory condition.

37. The system of claim 36, wherein the fourth routine is further adapted to generate an output indicative of a pneumothorax condition.

38. The system of claim 36, wherein the fourth routine is further adapted to generate an output indicative of a misplaced endotracheal tube.

39. The system of claim 29, wherein the third routine is further adapted to calculate a signal time delay between the first and second electrical signals and compare the signal time delay to a predetermined threshold value.

40. A method of detecting a respiratory condition within a body, the method comprising the steps of:
 receiving indigenous respiratory sounds adjacent to a first location on the body at a first time;
 converting the indigenous respiratory sounds received at the first time into a first electrical signal;
 generating a first set of frequency data using the first electrical signal; and using the first set of frequency data to calculate an energy ratio indicative of the respiratory condition.

41. The method of claim 40, wherein the step of using the first set of frequency data to calculate the energy ratio indicative of the respiratory condition includes the step of calculating the energy ratio indicative of the respiratory condition based on a first energy within a first band of frequencies and a second energy within a second band of frequencies.

42. The method of claim 41, wherein the step of calculating the energy ratio based on the first energy within the first band of frequencies and the second energy within the second band of frequencies includes the step of defining the first band of frequencies to include higher frequency components than the second band of frequencies.

43. The method of claim 40, further comprising the steps of:
receiving indigenous respiratory sounds adjacent to the first location on body at a second time,
converting the indigenous respiratory sounds received at the second time into a second electrical signal;
generating a second set of frequency data using the second electrical signal; and
using the second set of frequency data to calculate the energy ratio indicative of the respiratory condition.

44. The method of claim 43, wherein the step of receiving the indigenous respiratory sounds adjacent to the first location on the body at the first and second times includes the step of receiving respiratory sounds associated with one of a pair of lungs within the body.

45. The method of claim 43, wherein the step of receiving the indigenous respiratory sounds adjacent to the first location on body at the second time includes the step of receiving indigenous respiratory sounds prior to the existence of the respiratory condition.

46. The method of claim 40, further comprising the steps of:
receiving indigenous respiratory sounds adjacent to a second location on body;
converting the indigenous respiratory sounds received adjacent to the second location into a second electrical signal;
generating a second set of frequency data using the second electrical signal; and
using the second set of frequency data to calculate the energy ratio indicative of the respiratory condition.

47. The method of claim 46, wherein the step of receiving indigenous respiratory sounds adjacent to the first location on the body at the first time includes the step of receiving respiratory sounds associated with one of a pair of lungs within the body, and wherein the step of receiving indigenous respiratory sounds adjacent to the second location on the body includes the step of receiving respiratory sounds associated with the other one of the pair of lungs within the body.

48. A system for use in detecting a respiratory condition within a body, the system comprising:
a first transducer that converts indigenous respiratory sounds received adjacent to a first location on the body into a first electrical signal; and
a processing unit that generates a first set of frequency data using the first electrical signal and that uses the first set of frequency data to calculate an energy ratio indicative of the respiratory condition.

49. The system of claim 48, wherein the processing unit calculates the energy ratio indicative of the respiratory condition based on a first energy within a first band of frequencies and a second energy within a second band of frequencies.

50. The system of claim 49, wherein the first band of frequencies includes higher frequency components than the second band of frequencies.

51. The system of claim 48, wherein first location on the body is associated with one of a pair of lungs within the body.

52. The system of claim 48, further comprising a second transducer that converts respiratory sounds received adjacent to a second location on the body into a second electrical signal, and wherein the processing unit generates a second set of frequency data using the second electrical signal and uses the second set of frequency data to calculate the energy ratio indicative of the respiratory condition.

53. The system of claim 52, wherein the first and second locations adjacent to the body are associated with first and second respective lungs within the body.

54. A method of detecting a respiratory condition within a body, the method comprising the steps of:
impacting a portion of the body;
receiving vibrations resulting from the impact interacting with the respiratory condition and the impacted portion of the body;
converting the received vibrations into an electrical signal; and
using the electrical signal to calculate a value indicative of the respiratory condition.

55. The method of claim 54, wherein the step of using the electrical signal to calculate the value indicative of the respiratory condition includes the steps of calculating an envelope of the electrical signal and using the envelope to calculate a characteristic of the envelope of the electrical signal.

56. The method of claim 55, wherein the step of using the envelope to calculate the characteristic of the envelope of the electrical signal includes the steps of:
identifying a temporal location associated with a maximum amplitude of the envelope of the electrical signal;
identifying a portion of the envelope of the electrical signal surrounding the temporal location associated with the maximum amplitude of the envelope of the electrical signal; and
calculating the characteristic of the envelope of the electrical using the identified portion of the envelope of the electrical signal.

57. The method of claim 56, wherein the step of calculating the characteristic of the envelope of the electrical signal using the identified portion of the envelope of the electrical signal includes the steps of calculating a first time associated with an attack portion of the identified portion of the envelope of the electrical signal and calculating a second time associated with a decay portion of the identified portion of the envelope of the electrical signal.

58. The method of claim 56, wherein the step of calculating the characteristic of the envelope of the electrical signal using the identified portion of the envelope of the electrical signal includes the steps of fitting a curve to the identified portion of the envelope of the electrical signal and calculating a slope of the curve.

59. The method of claim 56, wherein the step of calculating the characteristic of the envelope of the electrical signal using the identified portion of the envelope of the electrical signal includes the step of determining the dominant frequency of the electrical signal.

60. The method of claim 56, wherein the step of calculating the characteristic of the envelope of the electrical signal using the identified portion of the envelope of the electrical signal includes the step of calculating a characteristic value associated with a pneumothorax condition.

61. A system for use in detecting a respiratory condition within a body, the system comprising:

an impact device that impacts a portion of the body to produce vibrations within the body;

a transducer that converts vibrations resulting from impacts to the portion of the body after the vibrations have interacted with the respiratory condition in the impacted portion of the body into an electrical signal; and a processing unit that uses the electrical signal to calculate a value indicative of the respiratory condition.

62. The system of claim 61, wherein the processing unit calculates an envelope of the electrical signal and uses the envelope of the electrical signal to calculate a characteristic of the envelope of the electrical signal.

63. The system of claim 62, wherein the processing unit:

identifies a temporal location associated with a maximum amplitude of the envelope of the electrical signal;

identifies a portion of the envelope of the electrical signal surrounding the temporal location associated with the maximum amplitude of the envelope of the electrical signal; and calculates the characteristic of the envelope of the electrical using the identified portion of the envelope of the electrical signal.

64. The system of claim 62, wherein the processing unit calculates a first time associated with an attack portion of the identified portion of the envelope of the electrical signal and a second time associated with a decay portion of the identified portion of the envelope of the electrical signal.

65. The system of claim 62, wherein the processing unit fits a curve to the identified portion of the envelope of the electrical signal and calculates a slope of the curve.

66. The system of claim 62, wherein the processing unit determines the dominant frequency of the electrical signal.

67. The system of claim 62, wherein the processing unit calculates a characteristic value associated with a pneumothorax condition.

* * * * *